US00PP27348P3

(12) United States Plant Patent
Brown

(10) Patent No.: US PP27,348 P3
(45) Date of Patent: Nov. 1, 2016

(54) ***DIANELLA* HYBRID PLANT NAMED 'DP401'**

(50) Latin Name: *Dianella prunina×caerulea*
Varietal Denomination: DP401

(71) Applicant: Graham Brown, Macquarie Fields (AU)

(72) Inventor: Graham Brown, Macquarie Fields (AU)

( * ) Notice: Subject to any disclaimer, the term of this patent is extended or adjusted under 35 U.S.C. 154(b) by 174 days.

(21) Appl. No.: 14/120,961

(22) Filed: Jul. 16, 2014

(65) Prior Publication Data

US 2016/0021808 P1 Jan. 21, 2016

(51) Int. Cl.
*A01H 5/12* (2006.01)

(52) U.S. Cl.
USPC ..... Plt./424

(58) Field of Classification Search
USPC ..... Plt./424
See application file for complete search history.

*Primary Examiner* — Keith Robinson
(74) *Attorney, Agent, or Firm* — Samuel R. McCoy, Jr.

(57) ABSTRACT

'DP401' is a distinctive hybrid cross between *Dianella prunina×caerulea* which is characterized by broad foliage texture, highly glaucous foliage, and high shoot density and uniformity of traits through successive cycles of asexual propagation.

2 Drawing Sheets

Latin name of the genus and species: The Latin name of the genus and species of the novel variety disclosed herein is *Dianella prunina×caerulea.*

Variety denomination: The inventive variety of *Dianella prunina×caerulea* disclosed herein has been given the variety denomination 'DP401'.

BACKGROUND OF THE INVENTION

The present invention relates to a new and distinct perennial variety of *Dianella prunina×caerulea*, which has been given the variety denomination of 'DP401'. Its market class is that of an ornamental plant or grass-like plant. 'DP401' is intended for use in landscaping and container gardening.

Parentage: In February 2009, seed that resulted from an open pollination of a *Dianella caerulea* 'DBB03' (U.S. Plant Pat. No. 17,998) and *Dianella prunina* 'DP303' (not patented) was collected from *Dianella prunina* 'DP303' plants and subsequently sown at a plant breeding facility in Cobbitty, New South Wales, Australia. Once rooted, the resulting progeny were planted in nursery pots, moved outdoors, and allowed to mature using standard nursery practices. Said progeny were regularly evaluated for improved performance and aesthetic characteristics. In August 2010, a selection resembling the male parent, 'DBB03', was made that exhibited broader foliage, a higher degree of foliage glaucosity, and higher shoot density when compared to either parent. The selection was given the name 'DP401'.

Asexual Reproduction: 'DP401' was first asexually propagated by dividing the root-bearing, rhizomatous propagules of the plant (i.e. "division cloning") in 2010 in Cobbitty, New South Wales, Australia and has since been asexually propagated through ten subsequent generations. The distinctive characteristics of the inventive 'DP401' variety are stable from generation to generation; clones of the variety produced by asexual reproduction maintain the distinguishing characteristics of the original plant.

SUMMARY OF THE INVENTION

'DP401' is a distinctive hybrid cross between *Dianella prunina×caerulea* which is characterized by broad foliage texture, highly glaucous foliage, and high shoot density and uniformity of traits through successive cycles of asexual propagation.

BOTANICAL DESCRIPTION OF THE PLANT

Figure 1:
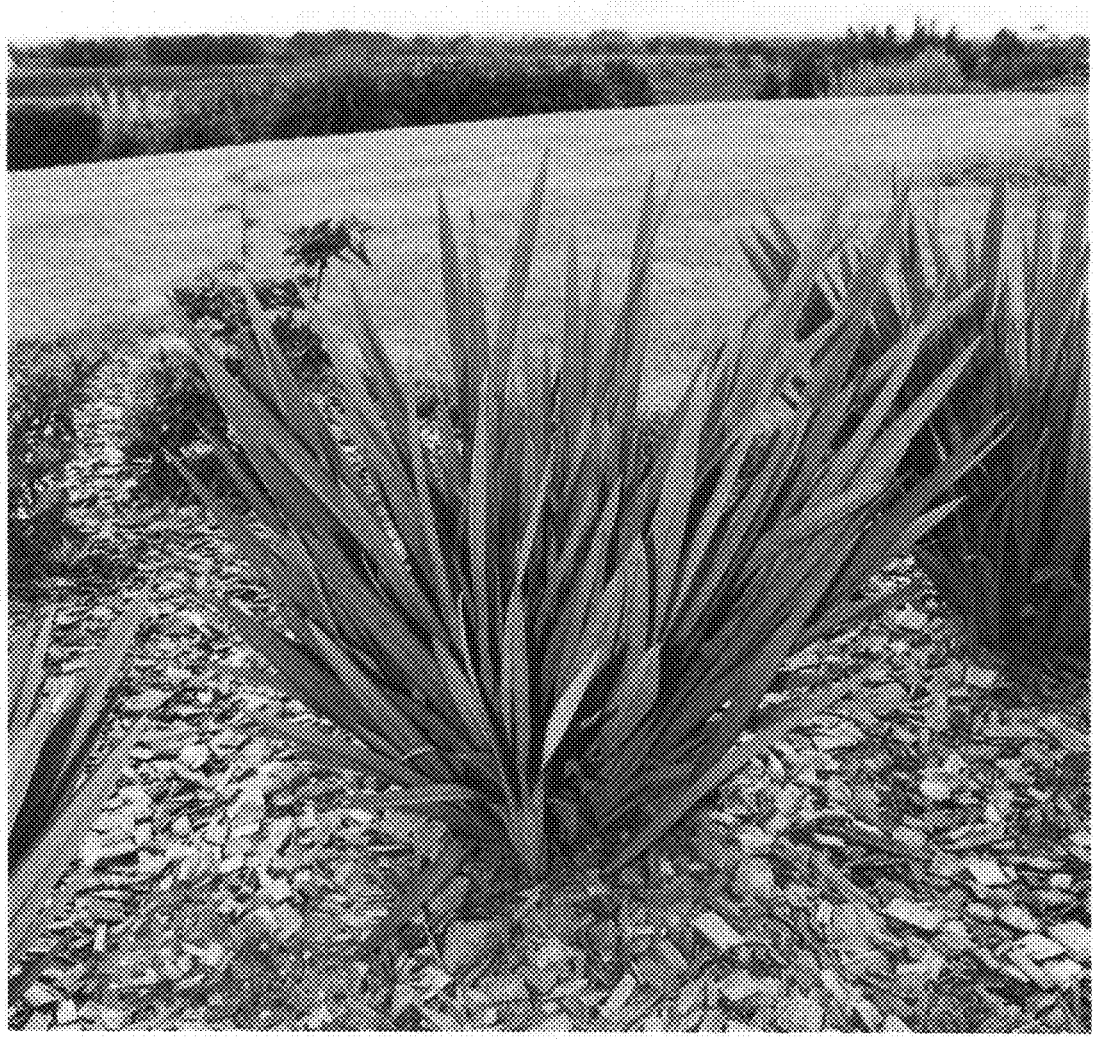
FIG. 1 illustrates an exemplary mature 'DP401' plant in the landscape at approximately two years of age.
Figure 2:
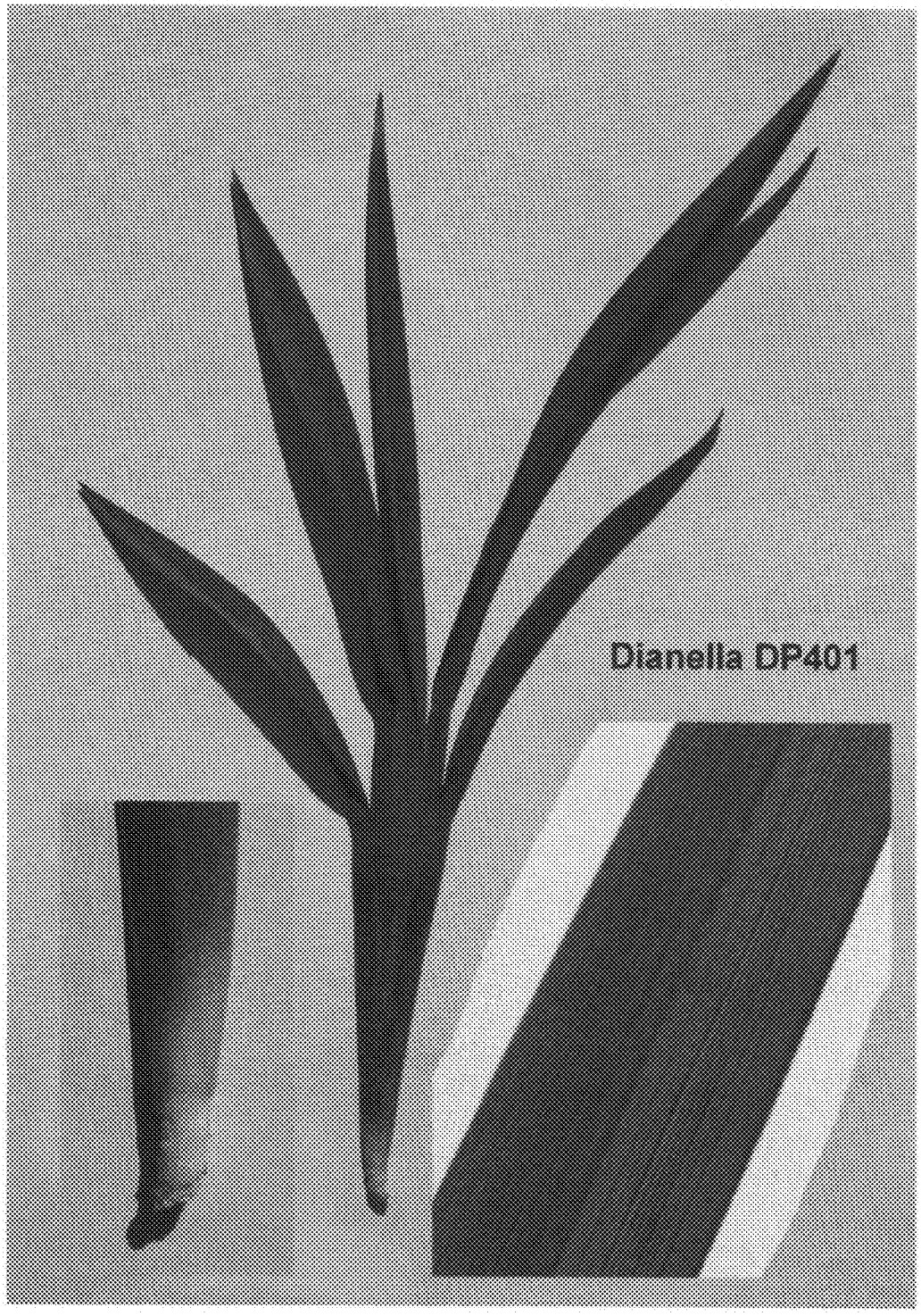
FIG. 2 illustrates the various foliage colors of 'DP401'.

The following is a detailed botanical description of a new and distinct variety of a *Dianella prunina×caerulea* ornamental plant known as 'DP401'. Plant observations were made on plants grown in Clarendon, New South Wales, Australia. Unless indicated otherwise, the descriptions disclosed herein are based upon observations made from mature one year old 'DP401' plants grown from rooted cuttings from May 2012 to May 2013 in 200 mm nursery pots filled with soilless potting media, maintained with granular slow release fertilizer, and regularly watered with overhead irrigation. No pest and disease measures were taken.

Those skilled in the art will appreciate that certain characteristics will vary with older or, conversely, younger plants. 'DP401' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Unless otherwise indicated, color notations are based on *The Royal Horticultural Society Colour Chart*, The Royal Horticultural Society, London, 2001 edition. Note that generic color descriptions such as 'blue' do not exist in the RHS charts and the corresponding RHS colors are quoted.

GROWTH HABIT, DIMENSIONS AND COLOR

Plant description:

*Plant habit.*—Erect, grass-like perennial.

*Height.*—60 cm.

*Width.*—60 cm.

*Bloom period.*—Spring in Cobbitty, New South Wales, Australia.

*Hardiness.*—USDA Zone 9 to 11.

*Environmental tolerances.*—'DP401' has not yet been observed under all conditions but has shown to be heat tolerant, adapting well to temperatures in excess of 100 degrees Fahrenheit without any noticeable damage. It has survived light to moderate frosts and temperatures down to 20 degrees Fahrenheit.

*Drought tolerance.*—'DP401' has not yet been observed under all conditions but it has shown excellent drought tolerance once established; typical of the species.

*Pest and disease susceptibility or resistance.*—No pest or disease measures were taken.

*Propagation.*—Propagation is accomplished by dividing the rhizomatous crown of the plant.

*Time to initiate roots.*—3 weeks at approximately 68 degrees Fahrenheit.

*Time to produce a rooted cutting.*—12 weeks at approximately 68 degrees Fahrenheit.

*Crop time.*—From 4 to 7 months are needed to produce a well-rooted 200 mm pot, starting from a rooted cutting, depending on geographic location.

Stem:

*Branching habit.*—Acaulescent, rhizomatous plant with shoots emerging upright at 90 degrees from rhizomes.

Roots: Short, subsurface rhizomes which root at nodes; roots fibrous; root density is high.

Basal shoots:

*Shoots density.*—Dense; more than 25 in a 200 mm nursery pot.

*Shoot strength.*—Strong.

*Cross section.*—Equitant.

*Shoot color.*—Combination of yellow-green 1478 and 146C while the base exhibits a combination of red-purple 62D and 63D.

*Shoot surface.*—Smooth.

Foliage:

*Type.*—Evergreen.

*Arrangement.*—Equitant.

*Division.*—Simple.

*Shape.*—Linear to Oblanceolate.

*Cross-section.*—Folded sharply inward along longitudinal axis, the adaxial surfaces of each side facing one another (i.e. keeled midrib).

*Apex.*—Acuminate.

*Base.*—Sheathed.

*Venation.*—Parallel.

*Vein color (adaxial surfaces).*—Same as surrounding foliage.

*Vein color (abaxial surfaces).*—Yellow green 147A (RHS 1986 edition), except for midrib which is greyed-red 180A (RHS 1986 edition).

*Margins.*—Serrulate; no spines are present.

*Attachment.*—Sessile.

*Surface texture (adaxial surface).*—Glabrous.

*Surface texture (abaxial surface).*—Glabrous.

*Mature leaf.*—Average length 60 cm, average width 2.2 cm.

*Leaf color (adaxial & abaxial surfaces).*—Both surfaces are closest to greyed-green 189A with the adaxial surface more glaucous than the abaxial surface. Margins appearing red in color, closest to 180A (RHS 1986 edition); no variegation is present; glaucosity is strong.

*Petiole.*—Leaves are sessile.

*Stipules.*—Absent.

Inflorescence:

*Type.*—Lax panicles sit above the foliage in late spring.

*Natural flowering season.*—Late spring in Cobbitty, New South Wales, Australia.

*Flowering habit.*—Inflorescence dimensions — Approximately 80 cm long and 35 to 40 cm wide. Inflorescence quantity — Potentially one inflorescence emerging from every shoot.

*Peduncle.*—Dimensions — Approximately 50 to 60 cm long and 1.5 mm wide at the base. Attitude — Upright. Color — Yellow-green RHS 144C. Texture and pubescence — Smooth; glabrous. Strength — Medium.

*Quantity of flowers per inflorescence.*—More than 100.

Bud:

*Dimensions.*—8 mm long and 4 mm wide.

*Shape.*—Ovoid; apex and base are obtuse.

*Color.*—A combination of greyed-purple RHS 186B and violet RHS 85B.

Flower:

*Flower type.*—Simple.

*Flower shape.*—Rotate; tepals are strongly reflexed.

*Diameter.*—Approximately 10 mm.

*Persistence.*—Not persistent.

*Flower aspect.*—Pendulous.

*Fragrance.*—Non-fragrant.

*Pedicels.*—Dimensions — 10 to 14 mm long and 2.0 mm wide. Color — Yellow-green RHS 144C, with slight intonations of greyed-purple RHS 186B. Texture and pubescence — Smooth; glabrous. Strength — Medium.

*Tepals.*—Quantity — Six. Arrangement — Whorled. Dimensions — 8 mm long and 3.5 mm wide. Fused or unfused — Unfused. Shape — Oblong. Margin — Entire; slightly undulate. Apex — Broad acute to obtuse. Base — Obtuse. Pubescence, texture, and luster — Glabrous, velvety; matte. Petal color when opening (upper side) — Violet RHS 85B. Petal color when opening (under side) — Violet RHS 85C. Petal color when fully opened (upper side) — Violet RHS 85B. Petal color when fully opened (under side) — Violet RHS 85C. Petal color fading to — Not fading.

Reproduction organs:

*Stamens.*—Quantity — Six. Anther — Attachment — Adnate. Shape — Narrowly oblong; apex is acute. Dimensions — 7.5 mm long and 2.0 to 2.5 mm wide. Color — Yellow RHS 9A. Filament — Dimensions — 2.5 mm long and 1.5 mm in diameter. Color — Yellow-white RHS 159D. Pollen — Light to medium density; black RHS 202A.

*Pistil.*—Quantity — One. Dimensions — 8.5 mm long and approximately 1 mm wide. Stigma — Shape —

Papillose swelling at the apex of the style. Dimensions — Approximately 1.5 mm in diameter and 1 mm tall. Color — Violet RHS 84C. Style — Dimensions — Approximately 7 to 8 mm long and 1 mm in diameter. Color — Violet RHS 84C. Ovary — Position — Superior. Dimensions — Approximately 3.5 mm in diameter and 2.5 mm tall. Color — Yellow-green RHS 144B.

Fruit and seed:

*Fruit*.—Shape — Globose. Dimensions — Approximately 9 mm long and 10 mm wide. Color — Violet-Blue RHS 89B to 89C. Texture and luster — Smooth and glossy.

*Seed*.—Quantity — Six. Shape — Ovoid Dimensions — 4 mm long and 1.5 mm wide. Color — Black RHS 202A.

COMPARISON OF 'DP401' WITH OTHER VARIETIES OF *DIANELLA CAERULEA*

There are no *Dianella pruninaxcaerulea* varieties known to the breeder, which would be available for comparison. However, when compared with the parents 'DP401' has several distinguishing characteristics.

The growth habit, leaf habit, texture and leaf color of 'DP401' more closely resembles that of the male parent, *Dianella caerulea* 'DBB03'. While both have greyed-green foliage corresponding closest to 189A, 'DP401' has a higher degree of glaucosity which translates to a more "silvered" appearance. Furthermore, the foliage of 'DP401' exhibits a greyed-red leaf margin corresponding to 180A whereas the foliage color along the leaf margin of 'DBB03' is greyed-green 189A. Also in 'DP401', the midrib on the abaxial leaf surface is also greyed-red 180A whereas the midrib of 'DBB03' is the same color as surrounding foliage. 'DP401' has broader foliage when compared to 'DBB03'. The foliage of 'DP401' averages 22 mm whereas the foliage of 'DBB03' is 15 mm at its widest point.

Compared to the female parent *Dianella prunina* 'DP303', 'DP401' has a different growth habit, higher shoot density, longer and slightly wider leaves and less anthocyanin expression in the foliage. 'DP401' has an erect growth habit whereas 'DP303' plants exhibit an arched to weeping habit. Mature 200 mm nursery pots of 'DP401' are observed to have greater than 25 shoots per pot whereas 'DP303' plants of the same age will have approximately 10 shoots per pot. Leaf blades of 'DP401' are measured at 60 cm long whereas mature leaves of 'DP303' are half as long at 30 cm. Widths are similar for both varieties, however 'DP303' is more deeply keeled at the midrib, with foliage sharply folded upward along the longitudinal axis, which creates the appearance of a more narrow leaf blade when compared to 'DP401'. While both have red leaf margins, the red pigments are more pronounced in 'DP303'. Leaf margins of 'DP401' are greyed-red 180A (RHS 1986 edition) whereas leaf margins of 'DP303' exhibit prominent red colorations corresponding to red-purple 61A to 61B.

That which is claimed is:

1. A new and distinct variety of *Dianella prunina*× *caerulea* plant named 'DP401', substantially as described and illustrated herein.

* * * * *